United States Patent [19]
Mellinger

[11] Patent Number: 5,697,929
[45] Date of Patent: Dec. 16, 1997

[54] SELF-LIMITING SET SCREW FOR USE WITH SPINAL IMPLANT SYSTEMS

[75] Inventor: Phillip A. Mellinger, Worthington, Ohio

[73] Assignee: Cross Medical Products, Inc., Columbus, Ohio

[21] Appl. No.: 544,884

[22] Filed: Oct. 18, 1995

[51] Int. Cl.⁶ .................................. A61B 17/56
[52] U.S. Cl. .................. 606/61; 606/72; 606/73; 411/5
[58] Field of Search ............... 606/72, 73, 61; 411/1, 393, 403, 5, 3, 4

[56] References Cited

U.S. PATENT DOCUMENTS

| | | |
|---|---|---|
| D. 200,217 | 2/1965 | Curtiss . |
| 791,548 | 6/1905 | Fischer . |
| 2,201,087 | 5/1940 | Hallowell . |
| 2,239,352 | 4/1941 | Cherry . |
| 2,295,314 | 9/1942 | Whitney . |
| 2,532,815 | 12/1950 | Kindsvatter . |
| 2,553,337 | 5/1951 | Shafer . |
| 2,778,265 | 1/1957 | Brown . |
| 2,877,681 | 3/1959 | Brown . |
| 2,927,332 | 3/1960 | Moore . |
| 3,115,804 | 12/1963 | Johnson . |
| 3,143,029 | 8/1964 | Brown . |
| 3,812,757 | 5/1974 | Reiland ............................ 411/5 |
| 4,492,500 | 1/1985 | Ewing ............................ 411/393 |
| 4,506,917 | 3/1985 | Hansen Arne ................. 411/393 |
| 4,763,644 | 8/1988 | Webb . |
| 4,764,068 | 8/1988 | Crispell . |
| 5,005,562 | 4/1991 | Cotrel . |
| 5,073,074 | 12/1991 | Corrigan et al. . |
| 5,129,388 | 7/1992 | Vignaud et al. . |
| 5,282,707 | 2/1994 | Palm ............................... 411/3 |
| 5,364,400 | 11/1994 | Rego, Jr. et al. ............... 606/72 |
| 5,382,248 | 1/1995 | Jacobson et al. .............. 606/61 |
| 5,499,892 | 3/1996 | Reed ............................... 411/5 |
| 5,507,747 | 4/1996 | Yuan et al. ..................... 606/61 |

FOREIGN PATENT DOCUMENTS

| | | | |
|---|---|---|---|
| 2467312 | 5/1981 | France ................................ 411/5 |
| 3738409 | 5/1989 | Germany .......................... 411/5 |
| 203508 | 9/1923 | United Kingdom ............. 411/393 |

*Primary Examiner*—Michael Buiz
*Assistant Examiner*—Julian W. Woo
*Attorney, Agent, or Firm*—Hudak & Shunk Co., L.P.A.

[57] ABSTRACT

The invention relates to a set screw having a self-limiting external torque head. The head has a hexagonal external cross-section and an internal bore which extends through a necked portion. The necked portion joins the external torque head to the threaded screw portion of the set screw. The necked portion has a cross-sectional thickness and strength to provide for shearing at a predetermined load limit, such as from about 54 to about 64 pounds per inch. The threaded screw portion has an internal hex to allow for the internal application of loosening torque at about two-thirds of the tightening torque limit, i.e., to provide a loosening torque of about 40 inch-pounds. The screw member includes a high-compression, rod-contacting surface such as a knurled surface.

21 Claims, 2 Drawing Sheets

SELF-LIMITING SET SCREW FOR USE WITH SPINAL IMPLANT SYSTEMS

FIELD OF THE INVENTION

The invention relates generally to set screws for use with spinal implant systems, and more particularly to a set screw having a head for the external application of torque which will shear at a predetermined load. The set screw further includes an internal opening for receiving a tool to permit the set screw to be removed.

BACKGROUND OF THE INVENTION

Spinal implant systems are used to strengthen, stabilize, and align the spine. Such systems often currently include an elongate stabilizer, such as a rod or plate; means to anchor the rod to a vertebra, such as a rod anchor, screw, or hook; and means to apply compression to the rod in order to hold it in place relative to the anchor. These compression means include external compression members (nuts or caps) and internal compression members (set screws or plugs).

Set screws are often used with various components of these systems to secure the components in position relative to one another. For example, the rod anchor may include a cap which twists or slides into position wherein a set screw is used to apply a compressive gripping force on the rod to hold it in position relative to the anchor. Some spinal systems include a closed anchor which encircles the rod wherein the set screw is used to lock the rod into position relative to the anchor. Set screws are also used to lock adjustable transverse links into position, and to lock the position of transversely adjustable rod-anchoring members.

Spinal implant systems are designed with the object of being able to apply and withstand relatively high mechanical forces so as to hold the spine in alignment while fusion takes place. However, it is also an object to provide a design which is as small as possible to provide minimal disruption to the biological environment. On the other hand, implant systems are designed with the goal of quick and efficient implantation during surgery. Therefore, the implant components need to be easy to assemble and large enough to enable the surgeon to easily handle them. Also the components need to interface well with the instrumentation to facilitate implantation and assembly during surgery.

Conventional prior art set screws require the use of a torque wrench to measure the amount of torque applied to the screw during assembly of the spinal implant system to assure that the set screw is engaged in the anchor tightly enough to hold the stabilizer securely in place relative to the anchor. If the surgeon overtightens the set screw, there is a risk of stripping the threads from the set screw; however, if the set screw is not tightened enough, the anchor may not have sufficient compressive grip on the stabilizer to enable the system to function properly.

The present invention therefore has an object of providing a set screw of a size which can be conveniently handled by the surgical staff during surgical implantation and which can be tightened to proper tightness without requiring the use of a torque wrench.

The invention has the further object of providing a means for the screw to be removed even after the head has been sheared from the screw. Therefore, the set screw in accordance with the present invention enables a surgeon to apply from about 50 to about 70 inch-pounds (6–8 Newton-meters) of torque to tighten the screw prior to the self-limiting shearing of the head at a preset maximum torque value. The set screw enables from about 35 to about 50 inch-pounds of loosening torque.

DETAILED DESCRIPTION OF INVENTION

Figure 3:
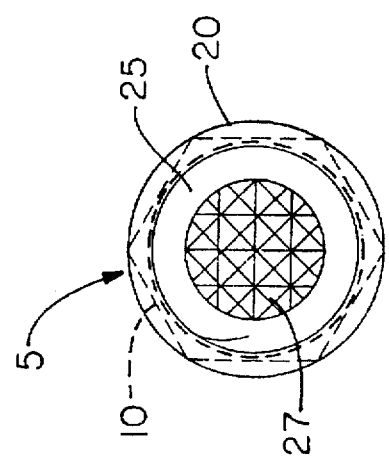
FIG. 3 is a bottom view of the set screw.
Figure 1:
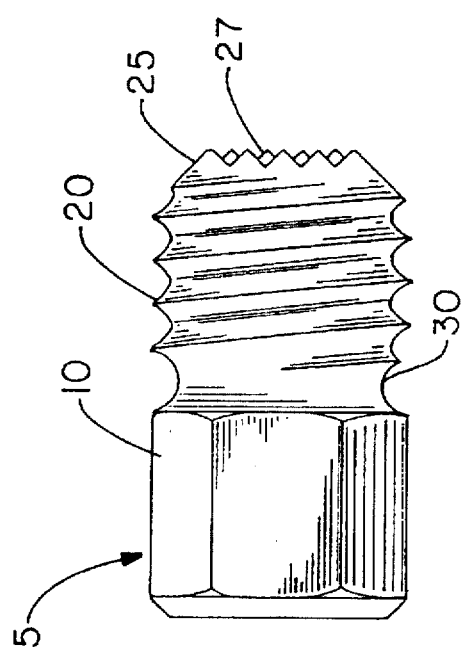
FIG. 1 is a side view of the set screw in accordance with the invention.
Figure 4:
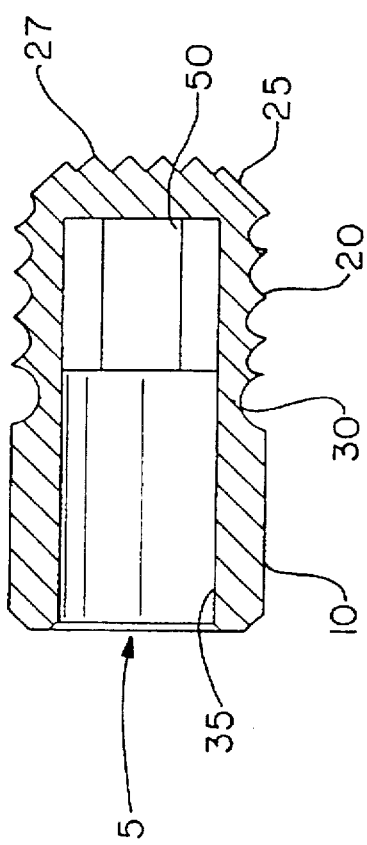
FIG. 4 is a cross-section of the set screw of the invention taken generally along line 4—4 of FIG. 2.
Figure 2:
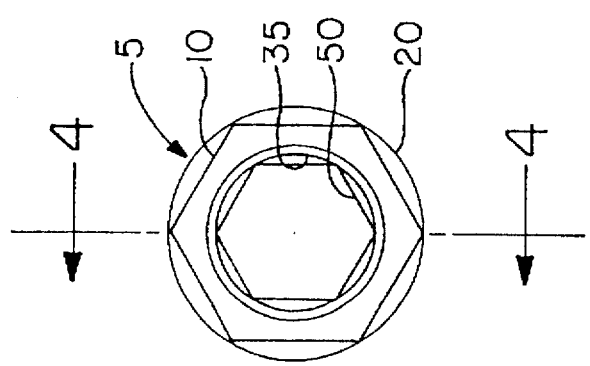
FIG. 2 is a top view of the set screw.

A set screw 5 in accordance with the invention is shown in FIG. 1 having a first externally threaded screw portion 20 and an axially aligned external torque or tightening head 10 joined to the screw portion 20 by a necked shearing area 30. By "external torque head" it is meant that the tightening torque is applied to the external surfaces of the head.

Figure 6:
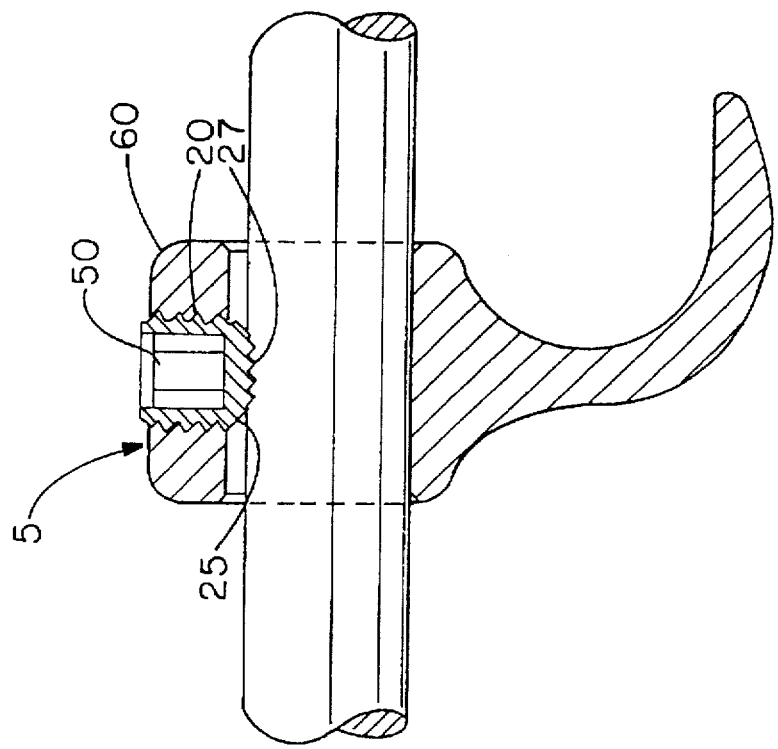
FIG. 6 is a view of the rod anchor and set screw after shearing.
Figure 5:
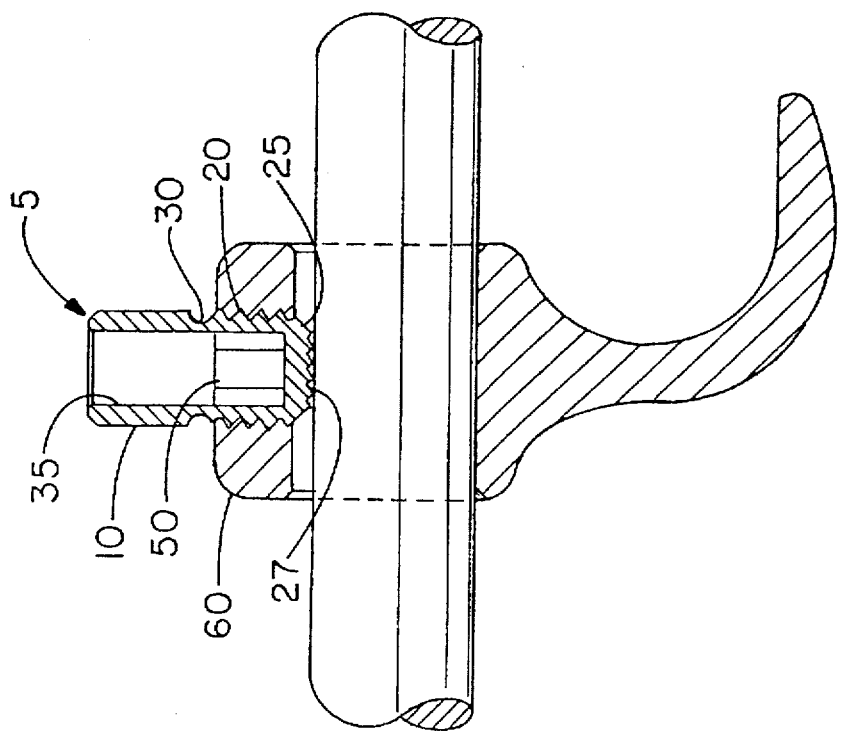
FIG. 5 is a view of the set screw in a rod anchor prior to shearing of the external torque-receiving head.

The torque head 10 has a shape and size which facilitates handling by the surgeon and which enables the external application of torque to tighten the set screw relative to a rod anchor (shown at 60 in FIGS. 5 and 6). Suitable cross-sectional shapes include triangular, square, pentagonal, hexagonal, octagonal, cross-shaped, and irregularly shaped configurations which would allow the transmission of a torquing force to the screw 5 to tighten it in place. The hexagonal cross-section is a particularly preferred shape.

The external torque head or tightening head 10 is dimensioned so as to transmit a predetermined torque level, i.e., more than about 45 or 50 inch-pounds and preferably 55 to 65 inch-pounds. The amount of torque which can be applied to the head prior to shearing will depend on the material as well as the cross-sectional area of the neck. Ideally, the head has an external diameter of from about 0.17 to about 0.25 inch, preferably from about 0.18 to about 0.20 inch and has a longitudinal length of from about 0.07 to about 0.17 inch, preferably from about 0.14 to about 0.16 inch.

For manufacturing purposes, it is convenient if the head 10 has a dimension comparable to the external diameter of the threaded screw portion 20. The torque head 10 is illustrated in the drawings as having a hexagonal external cross-section with a flat-to-flat measurement of about 0.12 to 0.25 inch and more specifically from about 0.14 to about 0.18 inch and with a point-to-point measurement of about 0.12 to about 0.25 inch with a preferred measurement of about 0.16 to about 0.19 inch.

The threaded portion 20 has a longitudinal length of from about 0.1 to about 0.25, and more specifically about 0.18 to about 0.20.

The threaded portion 20 has an external outer diameter of about 0.19 inch, a minor diameter of about 0.15 inch, and a thread pitch of about 28 to about 36, e.g., 32, threads per inch. The thread configuration is a standard, V-shaped thread. The screw portion 20 terminates in a bevel portion 25 which forms an angle of from about 40° to about 50° with respect to the longitudinal axis of the set screw. The screw portion includes a high-compression end 27 which has a rough surface. As shown, the high-compression surface 25 includes a raised diamond knurl with a pitch of about 0.025 inch to increase the compressive grip on the rod. As illustrated, the high-compression surface 27 is circular with a diameter of from about 0.08 to about 0.12 inch. The beveled edge has a longitudinal length of from about 0.03 to about 0.06 inch, and preferably about 0.04 to about 0.05 inch.

In accordance with the invention, a torque-limiting area 30 is provided to limit the application of tightening torque in order to protect the threaded area 20. More specifically, the torque-limiting area 30 comprises a necked portion having a longitudinal length of about 0.03 to about 0.05 inch and having a groove or radiused area which is designed to cause the torque applicator head 10 to shear at a predetermined load which is between 50 and 70 inch-pounds, preferably from 54 to 64 inch-pounds, in order to eliminate the need for a torque wrench to measure the tightening. Further, the necked area 30 is intended to shear evenly, i.e., in a way which will prevent an uneven break which could inhibit the insertion of a removal tool into the set screw or leave a jagged surface which could cause irritation to the patient.

In conjunction with the necked area 30, the torque head has an internal bore 35 which extends through the necked area 30 and which has a diameter to provide a residual cross-section of the set screw in the necked area to provide the predetermined load limit. For example, a suitable wall thickness is from about 0.015 to about 0.02 inch with an external diameter sized similarly to the minor diameter of the thread.

The threaded set screw portion includes an internal torque opening 50, such as a hexagonal bore. The internal torque applicator opening 50 is designed to allow loosening torques up to approximately 50 inch-pounds which is sufficient for the tightening torques which can be achieved for the present invention. By "internal torque opening" it is meant that the set screw has an opening which permits the internal application of a loosening torque. The internal opening 50 is intended to allow the application of a loosening torque that is approximately two-thirds of the tightening torque. The internal opening 50 of the torque head is illustrated as having a diameter slightly larger than the point-to-point distance of the hexagonal opening which can be achieved by manufacturing the set screw with a hexagonal opening which is subsequently drilled at a longitudinal depth through the necked portion in order to increase and make radially uniform the opening in the applicator.

The set screw of the present invention is illustrated in FIG. 5 in a rod anchor 60 with the applicator head still in place, and in FIG. 6 with a sheared applicator head. During surgery, however, the set screw would be loaded into the socket of a screwdriver which would receive the applicator head in order to install the set screw in its location. The instrument would be designed to grasp and hold the sheared head in order to avoid the head dropping into a wound. Further, the instrument may include means such as a spring-loaded C-clip which holds the set screw and which has a cavity into which the sheared head is transferred by a subsequently installed torque head of a subsequent set screw.

The surgeon can remove the set screw by seating a driver tool into the internal torque applicator opening, i.e., the internal hex, and reversing the direction of torque. The current invention increases the ease of removal of the set screw since the necked area inhibits the possibility of overtightening the screws and stripping the threads of the set screw.

The set screw is made of a sufficiently hard biocompatible material such as, for example, hardened, surgical-grade stainless steel, e.g., 22-13-5 stainless steel. Other appropriate materials such as titanium or biocompatible plastics or composites may be used with the appropriate revision to the prescribed predetermined load limit and rates of compression.

A static axial slip test was performed using a closed rod anchor with both annealed and unannealed rods and shear head set screws in accordance with the invention. The amount of load applied to cause 0.012 inch of axial slip was measured for four samples each of annealed rods and unannealed rods.

For the annealed rods, the mean axial slip value was 376.4 pounds; the mean value of shear-off torque was 59 inch-pounds with a S.D. of 2 inch-pounds; and the set screw removal torque mean value was 42 inch-pounds with a S.D. of 4 inch-pounds. (This value was measured after the axial slip test and may have been effected by that test.)

For the unannealed rods, the axial slip failure load mean value was 342.5 pounds; the mean shear-off torque for these samples was 61 inch-pounds with a S.D. of 1 inch-pound; and the set screw removal torque mean value after axial slip was 35 inch-pounds with an S.D. of 2 inch-pounds.

The testing revealed that the set screw of the invention with the rod anchor achieves a desirable compressive loading on the rod by achieving satisfactory tightening and loosening torque values.

While in accordance with the patent statutes the best mode and preferred embodiment has been set forth, the scope of the invention is not limited thereto, but rather by the scope of the attached claims.

What is claimed:

1. A spinal implant set screw comprising a torque head having at least one planar external surface for the external application of torque to said set screw, said planar external surface being parallel to the longitudinal axis of said set screw, and said torque head joined by a torque-limiting area to a screw member having an external threaded area which has an internal torque opening.

2. A spinal implant set screw as set forth in claim 1, wherein said torque-limiting area comprises a necked portion.

3. A spinal implant set screw as set forth in claim 1, wherein said torque-limiting area further includes an internal opening.

4. A spinal implant set screw as set forth in claim 1, wherein said torque-limiting area has a reduced cross-sectional area.

5. A spinal implant set screw as set forth in claim 1, wherein said internal torque opening comprises a hexagonal opening.

6. A spinal implant set screw as set forth in claim 4, wherein said screw member has a high-compression surface.

7. A spinal implant set screw as set forth in claim 6, wherein said high-compression surface is a knurled surface.

8. A spinal implant set screw as set forth in claim 7, wherein said screw member has a bevel and a lateral surface with said knurled surface.

9. A spinal implant set screw as set forth in claim 8, wherein said external torque head comprises a head having an external hexagonal cross-section.

10. An orthopedic set screw having a torque head having at least one external planar surface for the external application of torque, said external planar surface being parallel to the longitudinal axis of said set screw, and said torque head joined by a torque-limiting area to a screw member having external threads, said torque-limiting area being an area of reduced external diameter and including a central opening, said screw member including an torque applicator opening adjacent said central opening and internal to said external threads and including an external, high-compression, rod-contacting surface.

11. An orthopedic set screw as set forth in claim 10, which comprises a biocompatible, surgical-grade metal.

12. An orthopedic set screw as set forth in claim 11, wherein said applicator head shears at said torque-limiting area at a torque of from about 54 to about 64 inch-pounds and said internal torque applicator area allows a loosening torque of up to about 50 inch-pounds.

13. Am orthopedic set screw as set forth in claim 12, wherein said torque applicator head has an external cross-sectional hexagonal shape and said torque applicator opening has an internal hexagon cross-section.

14. A surgical screw having a longitudinal axis and a first threaded portion having a knurled terminal surface, and an axially aligned second portion with a hexagonal-shaped external configuration, said screw having an opening along said longitudinal axis which is hexagonal-shaped in at least said first threaded portion.

15. A spinal implant system, comprising;

a rod;

an anchor which cooperates with said rod and having a threaded bore; and a set screw having a longitudinal axis and which is received in said threaded bore to secure said rod relative to said anchor and comprising a hexagonal shaped torque head having a first diameter joined by a torque-limiting area to a screw member having external threads of a second diameter, said torque-limiting area having a third diameter which is smaller than the first diameter and smaller than the second diameter and the first and second diameter may be the same or different and the torque-limiting area having a central opening, said screw member including a hexagonal shaped torque applicator opening joined to said central opening and internal to said externally threaded area.

16. A spinal implant system, comprising:

a rod;

an anchor which cooperates with said rod and has a threaded bore; and a set screw which is received in said threaded bore to secure said rod relative to said anchor, said set screw having a longitudinal axis and having along said axis a torque head, a torque-limiting area, and an externally threaded area which includes a terminal high compression rod-contacting surface, said torque-limiting area having a smaller external diameter than said torque head, and said torque head extending axially outward relative to said threaded bore, said set screw further comprising an internal torque opening extending along said longitudinal axis through said torque head and said torque-limiting area into said externally threaded area.

17. A spinal implant system according to claim 16, wherein said torque head is an external torque head.

18. A spinal implant system according to claim 17, wherein said external torque head comprises a head having an external hexagonal cross-section.

19. A spinal implant system according to claim 16, wherein said internal torque opening comprises a hexagonal opening.

20. A spinal implant system according to claim 16, which comprises a biocompatible, surgical-grade metal.

21. A spinal implant system according to claim 20, which comprises a biocompatible, surgical-grade metal.

* * * * *

Adverse Decisions in Interference

Patent No. 5,697,929, Phillip A. Mellinger, SELF-LIMITING SET SCREW FOR USE WITH SPINAL IMPLANT SYSTEMS, Interference No. 104,246, final judgment adverse to the patentee rendered April 27, 1999, as to claims 1-14 and 15-21.
*(Official Gazette June 8, 1999)*